(12) United States Patent
Roscher et al.

(10) Patent No.: US 8,907,123 B2
(45) Date of Patent: Dec. 9, 2014

(54) PROCESS FOR THE ACETOXYLATION OF OLEFINS IN THE GAS PHASE

(75) Inventors: Anja Roscher, Munich (DE);
Hans-Juergen Eberle, Munich (DE);
Roland Heidenreich, Munich (DE);
Herbert Jung, Munich (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 14/240,945

(22) PCT Filed: Aug. 23, 2012

(86) PCT No.: PCT/EP2012/066390
§ 371 (c)(1),
(2), (4) Date: Feb. 25, 2014

(87) PCT Pub. No.: WO2013/030073
PCT Pub. Date: Mar. 7, 2013

(65) Prior Publication Data
US 2014/0194649 A1     Jul. 10, 2014

(30) Foreign Application Priority Data
Aug. 30, 2011   (DE) .......................... 10 2011 081 786

(51) Int. Cl.
*C07C 67/05* (2006.01)
*C07C 67/055* (2006.01)

(52) U.S. Cl.
CPC .............. *C07C 67/05* (2013.01); *C07C 67/055* (2013.01)
USPC .......................................................... 560/245

(58) Field of Classification Search
None
See application file for complete search history.

(56) References Cited

U.S. PATENT DOCUMENTS

| 5,179,056 A | 1/1993 | Bartley |
| 6,399,813 B1 | 6/2002 | Blum et al. |
| 6,448,432 B2 * | 9/2002 | Williams ...................... 560/245 |
| 2008/0194844 A1 * | 8/2008 | Guckel et al. ................. 549/248 |
| 2009/0054683 A1 | 2/2009 | Bueker et al. |
| 2010/0022796 A1 | 1/2010 | Heidenreich et al. |

FOREIGN PATENT DOCUMENTS

| WO | 2006/042659 A1 | 4/2006 |
| WO | 2007101749 A1 | 9/2007 |
| WO | 2008071610 A2 | 6/2008 |

* cited by examiner

*Primary Examiner* — Sudhakar Katakam
(74) *Attorney, Agent, or Firm* — Brooks Kushman P.C.

(57) ABSTRACT

Yield and selectivity of olefin acetoxylation are improved through the use of successive catalyst zones of different reactivities, the successive zones contained in one or more reaction tubes arranged is parallel.

9 Claims, 2 Drawing Sheets

PROCESS FOR THE ACETOXYLATION OF OLEFINS IN THE GAS PHASE

CROSS-REFERENCE TO RELATED APPLICATIONS

This application is the U.S. National Phase of PCT Appln. No. PCT/EP2012/066390 filed Aug. 23, 2012, which claims priority to German application DE 10 2011 081 786.7 filed Aug. 30, 2011, the disclosures of which are incorporated in their entirety by reference herein.

BACKGROUND OF THE INVENTION

1. Field of the Invention

The present invention relates to a process for the acetoxylation of olefins, in which a gaseous reaction stream containing an olefin, acetic acid and molecular oxygen is passed over at least two catalyst zones of differing reactivity arranged in series. Furthermore, the invention relates to a catalyst system for the gas-phase oxidation of olefins to form acetoxylated products, in particular for the preparation of vinyl acetate, which comprises at least two catalyst zones which are arranged in layers and have a reactivity matched to the course of the reaction.

2. Description of the Related Art

Processes for the acetoxylation of ethylene in the gas phase are of particular industrial interest. It is known from the literature that acetoxylations can be carried out industrially by catalytic gas-phase oxidation of olefins such as ethene or propene in fixed-bed reactors. These reactions are preferably carried out in shell-and-tube reactors. Unsaturated esters such as vinyl acetate, inter alia, are prepared by means of this reaction. In general, this reaction is carried out by passing a gaseous mixture comprising molecular oxygen, an olefin and acetic acid through a reactor. Use is usually made of a shell-and-tube reactor in which a plurality of reaction tubes are arranged in parallel and in each of which a uniform catalyst charge is located. The excess heat of reaction involved is removed by means of a heat transfer medium. An example of such a reactor is a boiling water reactor.

As catalytically active components of the catalysts used here, it is possible to use, inter alia, palladium and/or compounds thereof and alkali metal compounds and also additionally gold and/or compounds thereof (Pd/alkali metal/Au system). Systems composed of cadmium and/or compounds thereof (Pd/alkali metal/Cd system) or barium and/or compounds thereof (Pd/alkali metal/Ba system) and also systems containing palladium, alkali metal compounds and mixtures of gold and/or cadmium and/or barium are also used. All these systems are usually present on a suitable support material. Industrially, preference is given to using palladium/gold catalyst systems.

As alkali metal compounds, use is usually made of potassium compounds, for example potassium acetate. During operation, introduction of the alkali metal compound is usually carried out in order to compensate corresponding alkali metal losses within the catalyst bed.

Despite various methods of regulating the reaction temperature known from the prior art, local formation of a stationary temperature peak in the catalyst bed in which a higher temperature prevails than in the remainder of the catalyst bed can occur.

These temperature peaks (known as "hot spots") bring about a series of undesirable effects during the course of the reaction. Firstly, they limit a further increase in the starting material concentration (loading), which is equivalent to limitation of the space-time yield, and secondly an increase in total oxidation in the reaction mixture can occur (reduction in selectivity to the target product). The latter is, in particular, reflected in a higher specific raw material usage and has a significantly negative effect on the economics of the process. Furthermore, hot spots bring about premature aging of the catalyst.

Particularly in the case of fresh catalyst beds and also in the case of reactions with a high oxygen loading, irreversible damage to the catalyst can occur in this sensitive range when heat removal is insufficient.

Furthermore, a decrease in the starting material concentration combined with a simultaneous increase in the product concentration occurs as the reaction progresses along the catalyst bed. The increasing product concentration can then again lead to inhibition of product formation and thus to a decrease in selectivity and conversion.

Processes for the acetoxylation of ethylene in the gas phase which lead high yields of vinyl acetate are of great economic importance.

WO 2008/071610 discloses a process and a catalyst system comprising a catalyst which comprises palladium, gold and potassium acetate and is applied to an $SiO_2$ support having a large surface area and can be operated at a space-time yield of more than 800 [g (VAM)/l cat*h] at ethene selectivities of greater than 92% and at a low degree of formation of ethyl acetate relative to vinyl acetate.

U.S. Pat. No. 5,179,056 discloses a process for preparing vinyl acetate by reaction of ethylene and acetic acid in the presence of an oxygen-containing gas over a highly reactive palladium/gold coated catalyst.

U.S. Pat. No. 6,399,813 discloses a highly active fluidized-bed vinyl acetate catalyst on a support composed of inert microspheroidal particals composed of silicon oxide, zirconium oxide or aluminum oxide and having a defined pore distribution.

In view of the great economic importance of acetoxylated products and the high-performance catalysts known from the prior art, there is a great need to optimize the course of the reaction in respect of conversion, selectivity and life of the catalyst.

WO 2007/101749 and WO 2006/042659 disclose, for example, synthesis reactors for preparing vinyl acetate monomer with increased selectivity and productivity, in which gaseous ethylene and acetic acid and also an oxygen-containing gas react catalytically, with the synthesis reactors being a wall reactor and the catalytic synthesis being carried out in a plurality of reaction spaces and at least one wall of the reaction spaces being coated with catalyst and at least one wall of the reaction spaces being indirectly cooled.

Reactions which describe a series arrangement of at least two reactors which can be charged with catalysts of differing reactivity are likewise known from the prior art. However, a disadvantage of this arrangement is the large outlay in terms of equipment.

It was an object of the invention to provide a novel process for the acetoxylation of acetic acid using a catalyst system by means of which, in particular, high space-time yields, high selectivities with low by-product formation and an ideally isothermal temperature profile in the catalyst bed are achieved, as a result of which a lengthening of the life and also short start-up times of fresh catalyst can be achieved and at the same time the use of conventional shell-and-tube reactors can be retained.

SUMMARY OF THE INVENTION

It has now been surprisingly found that the use of a catalyst system comprising at least two catalyst zones which have differing reactivity and are arranged in layers in the flow direction enable achievement of a higher space-time yield, better selectivities with low by-product formation, combined with a virtually isothermal temperature profile in the catalyst bed.

BRIEF DESCRIPTION OF THE PREFERRED EMBODIMENTS

DETAILED DESCRIPTION OF THE PREFERRED EMBODIMENTS

Figure 1:
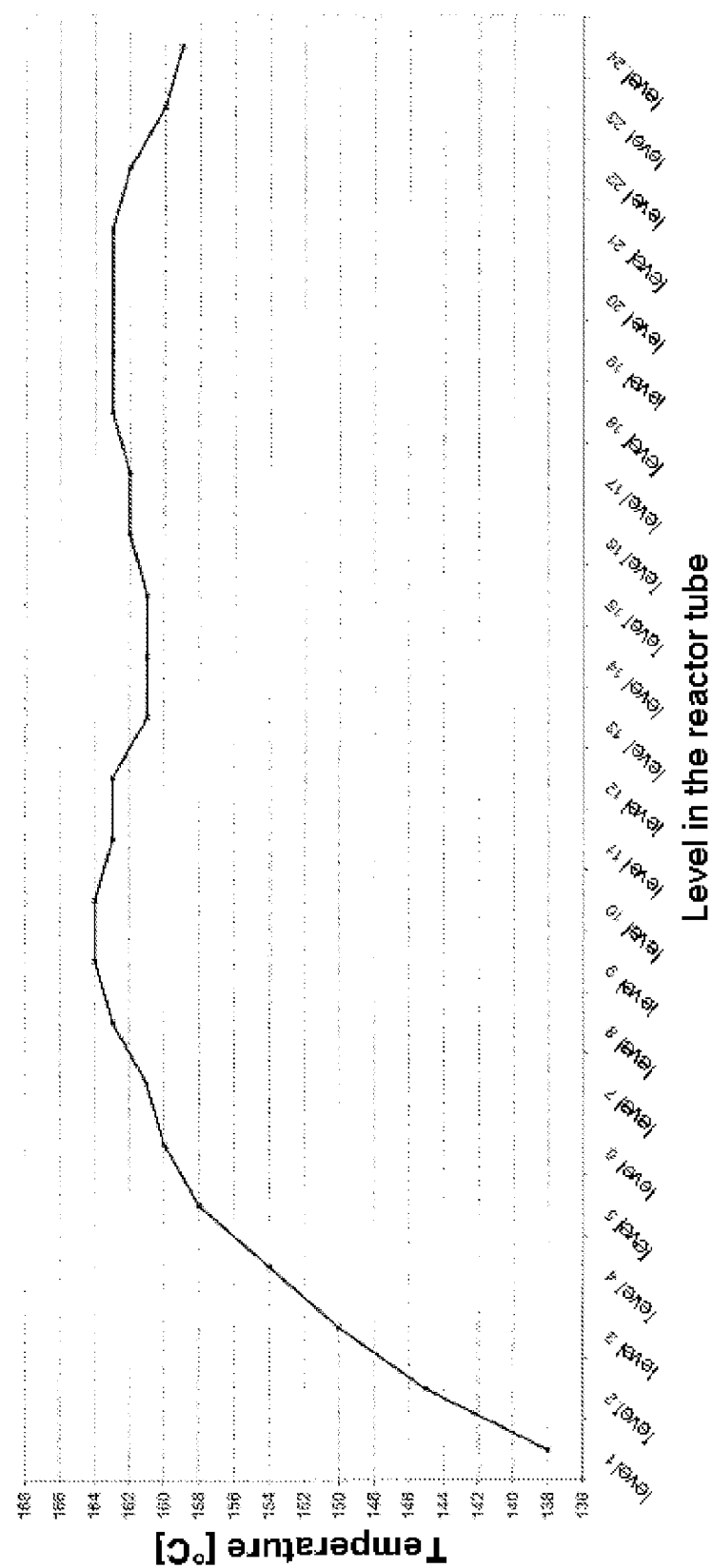
FIG. 1 illustrates the temperature profile of an inventive acetoxylation reactor having two catalyst beds of different activity.

The invention provides a process for the acetoxylation of olefins in a gaseous reaction stream containing an olefin, acetic acid and an oxygen-containing gas, wherein the reaction gas is passed over at least two catalyst zones of differing reactivity arranged in series, where the catalyst zones are located in one or more reaction tubes arranged in parallel.

As an oxygen-containing gas, preference is given to using molecular oxygen.

The process of the invention can be used for preparing unsaturated esters from olefins, organic acids and oxygen in the gas phase. In particular, it can be used for the production of vinyl acetate monomer. For this purpose, ethene, acetic acid and molecular oxygen or air are reacted in the gas phase, optionally with addition of inert gases, at temperatures of from 100 to 250° C. and at atmospheric or superatmospheric pressure, for example from 1 to 25 bar, in the presence of the multi-zone catalyst systems according to the invention. Typically, space velocities of the gas phase of from 1000 to 10,000 standard liters of gas mixture per liter of catalyst and per hour are achieved in industrial shell-and-tube reactors.

In the process for preparing vinyl acetate monomer, the catalyst system having differing activities of the individual catalyst zones can, compared to a conventional uniform catalyst zone of a particular activity, be run up quickly to a high space-time-yield with a significantly improved selectivity. According to the prior art, uniform catalysts having a uniform activity usually attain their final level only after days or weeks.

The arrangement according to the invention of the catalyst can also be used for the acetoxylation of olefins such as propene.

It has surprisingly been found that even the juxtaposition of two catalyst zones having differing activities leads to a significant increase in the space-time yield and selectivity in the preparation of, in particular, vinyl acetate from ethene, acetic acid and oxygen in the gas phase. According to the invention, at least two catalyst zones having differing activity are juxtaposed. A juxtaposition of more than two zones is likewise possible and part of the present invention.

The catalyst zone nearest the gas entry end preferably has a lower activity and the adjoining catalyst zones have an increasing activity in order through to the gas exit end.

The presence of a relatively low-activity catalyst zone at the gas entry end makes it possible to achieve a considerable shortening of the time required on first start-up of the catalyst to reach the desired maximum space-time yield under stable operating conditions.

It is unimportant in the process of the invention for using a multi-zone catalyst whether the catalyst is present in the form of a catalyst bed (for example a fixed-bed catalyst in a shell-and-tube reactor) or is applied in the form of individual regions (for example relatively thin catalyst coatings in a microstructure).

A particularly preferred embodiment of the invention is the juxtaposition of three catalyst zones, with the first catalyst zone nearest the gas entry end having the lowest activity, compared to the second and third catalyst zones located nearer the gas exit end and the third catalyst zone having the highest activity. This catalyst system having an activity gradient from the gas entry end to the gas exit end leads to further considerable improvements in respect of space-time yield and selectivities.

To control the activity of the individual catalyst zones, it is possible to use one or more of the following measures:

a.) variation of the content of activity-controlling promoters in the catalyst (potassium acetate, lithium acetate, sodium acetate, cesium acetate, rubidium acetate or mixtures of these)

b.) use of different metal contents of gold, palladium, cadmium based on the catalyst support c.) variation of the mixing ratio of the noble metals, for example Pd:Au d.) use of different BET surface areas of the catalyst supports used e.) use of various bulk densities of the catalyst supports f.) use of various catalyst support geometries g.) use of different metal dispersions h.) dilution of a vinyl acetate monomer catalyst which is too active/"super-active" by means of inert material i.) use of a differing acidity and/or hydrophilicity of the catalyst support j.) variation of the thickness of the active noble metal layer on the catalyst support.

As support shapes for the catalysts used, it is possible to use all geometries known to those skilled in the art, for example spheres, cylinders, rings, shaped bodies having one or more through-channels, crown rings, wagon wheels, monoliths, trilobes or tetralobes.

Particular shaped catalyst bodies, for example rings, crown rings, rings having a plurality of through-channels, make low pressure drops and low bulk densities possible.

In an embodiment of the invention, various geometries of shaped catalyst bodies are used in the multi-zone catalyst system. Particular preference is given to an embodiment in which one or more catalyst zones comprise rings having a wall thickness of less than 2 mm, more preferably less than 1 mm.

The heat management can be adapted particularly well with the aid of multi-zone catalyst systems and different shaped catalyst body geometries, as a function of the tube geometry of the reactor.

In particular, VAM catalysts on $SiO_2$ supports or mixed oxide supports are used, with the metal oxides used being able to be of natural origin, e.g. bentonites, or be pyrogenically produced. Particular preference is given to $SiO_2$ supports, in particular $SiO_2$ supports based on pyrogenic silica. Furthermore, it is possible for these supports to be modified by targeted doping or to be pretreated by washing.

As catalyst supports, it is possible to use high surface area, high-purity silicon dioxide supports as described in WO 2008/071610 (incorporated by reference) which have BET surface areas in the range from 30 $m^2/g$ to 500 $m^2/g$. It is likewise possible to use $SiO_2$ materials which have been doped in a targeted way with metals.

For the synthesis of vinyl acetate monomers, it is advantageous to provide the catalyst with from 0.1 to 5.0% by weight of palladium and from 0.2 to 3.5% by weight of gold or from 0.1 to 3.5% by weight of cadmium or from 0.1 to 3.5% by weight of barium and from 0.5 to 15% by weight of alkali metal, in each case based on the weight of the support used. The loadings can vary as a function of the type of catalyst used (Pd/Au type, Pd/Cd type or Pd/Ba type).

The palladium content of the Pd/alkali metal/Au catalysts is from 0.2 to 5.0% by weight, preferably from 0.3 to 3.0% by weight.

The gold content of the Pd/alkali metal/Au catalysts is from 0.2 to 5.0% by weight, preferably from 0.3 to 3.0% by weight.

The alkali metal content of the Pd/alkali metal/Au catalysts is from 0.5 to 15% by weight, preferably from 1.0 to 10% by weight.

The palladium content of the Pd/alkali metal/Cd or Pd/alkali metal/Ba catalysts is from 0.1 to 5% by weight, preferably from 0.2 to 4.0% by weight.

The cadmium content of the Pd/alkali metal/Cd catalysts is from 0.1 to 3.5% by weight, preferably from 0.2 to 3.0% by weight.

The barium content of the Pd/alkali metal/Ba catalysts is from 0.1 to 3.5% by weight, preferably from 0.2 to 3.0% by weight. The Ba content here is preferably in the same range as the Cd content in the case of Cd types.

The alkali metal content of the Pd/alkali metal/Cd or Pd/alkali metal/Ba catalysts is from 0.3 to 15% by weight, preferably from 0.5 to 10% by weight.

The invention is illustrated by the following examples.

General Test Conditions:

Activity and selectivity of the catalysts in the following examples and comparative examples are measured over a time of up to 200 hours. The catalysts are tested in a flow tube whose temperature is controlled by means of oil (reactor length 1200 mm, internal diameter 19 mm) at an absolute pressure of 9.8 bar and a space velocity (GHSV) of 4000-5000 standard $m^3/(m^3*h)$ using the following gas composition: 60% by volume of ethene, 19.5% by volume of argon, 13% by volume of acetic acid and 7.5% by volume of oxygen. The catalyst systems are tested in the temperature range from 130 to 180° C. (gas entry temperature upstream of the catalyst bed). To characterize the course of the reaction, the temperature profile is measured by means of a multi-point temperature sensor in the catalyst bed. The reaction products and unreacted starting materials are analyzed at the output of the reactor by means of on-line gas chromatography. The space-time yield of the catalyst system in gram of vinyl acetate monomer per hour and liter of catalyst (g (VAM)/l of cat.*h) is determined as a measure of the catalyst activity. The selectivity is determined via the ratio of vinyl acetate formed to ethene reacted.

In addition to determination of the reaction products in the gas phase, the liquid reaction products are condensed in a vessel maintained at from 10 to 15° C. and the condensate obtained is analyzed by means of gas chromatography.

Production of the Catalysts:

The production and characterization of the individual catalysts for the examples and comparative examples is comprehensively described in WO 2008/071610. The BET surface area of the catalyst supports is determined in accordance with DIN 66131 using nitrogen.

The fill heights indicated for the individual zones are based on the total length (100%) of the test reactor described. Depending on the dimensions of the reactor tube, other optimum fill heights may be specified.

The designations of the catalyst zones are based on the position in the flow direction of the gas, with the first zone being the catalyst zone as the gas inlet of the reactor.

For the multi-zone catalyst system according to the invention, it is immaterial whether the reactants flow from the bottom upward or from the top downward in a reactor (for example an upright shell-and-tube reactor).

EXAMPLE 1

Pd/Au Type Catalyst with Differing Promoter Contents

For this purpose, a catalyst was produced as described in WO 2008/071610 with the exception that the catalyst of the $1^{st}$ zone contains 6.5% by weight of potassium and the catalyst in the $2^{nd}$ zone contains 3.0% by weight of potassium.

| Designation | $1^{st}$ Zone | $2^{nd}$ Zone | $3^{rd}$ Zone |
|---|---|---|---|
| relative length [%] | 50 | 50 | — |
| SiO$_2$ support BET (m$^2$/g) | 200 | 200 | — |
| Pd (% by weight) | 2.0 | 2.0 | — |
| Au (% by weight) | 2.0 | 2.0 | — |
| K (% by weight) | 6.5 | 3.0 | — |

This catalyst system according to the invention makes it possible to achieve maximum space-time yields of 980 g (VAM)/l of cat.*h at maximum ethene selectivities of 93.2% in the test in the reactor under the conditions described.

EXAMPLE 2

Pd/Au Type Catalyst Having Differing Support BET Surface Areas and Promoter Contents Two catalysts were synthesized as described in WO 2008/071610; these differed in that the catalyst in the $1^{st}$ zone was produced on SiO$_2$ supports having a BET surface area of 150 m$^2$/g and a potassium content of 6.5% by weight and the catalyst in the $2^{nd}$ zone was produced on SiO$_2$ supports having a BET surface area of 220 m$^2$/g and a potassium content of 3.0% by weight.

| Designation | $1^{st}$ Zone | $2^{nd}$ Zone | $3^{rd}$ Zone |
|---|---|---|---|
| relative length [%] | 50 | 50 | — |
| SiO$_2$ support BET (m$^2$/g) | 150 | 220 | — |
| Pd (% by weight) | 2.0 | 2.0 | — |
| Au (% by weight) | 2.0 | 2.0 | — |
| K (% by weight) | 6.5 | 3.0 | — |

This catalyst system according to the invention makes it possible to achieve maximum space-time yields of 1050 g (VAM)/l of cat.*h at maximum ethene selectivities of 93.5% in the test in the reactor under the conditions described. FIG. 1 shows the temperature profile of this two-zone catalyst system with a largely isothermal temperature profile with optimized catalyst utilization in the downstream region of the reactor. FIG. 1 shows the temperature profile at 7.5% by volume of $O_2$, 4500 standard $m^3/(m^3*h)$ and a gas entry temperature of 138° C.

EXAMPLE 3

Pd/Au Type Catalyst with Differing EM Contents

Two catalysts were synthesized as described in WO 2008/071610; these differed in that the catalyst in the $1^{st}$ zone was produced on $SiO_2$ supports having a BET surface area of 180 $m^2/g$ and a Pd and Au content of 2.0% by weight in each case and the catalyst in the $2^{nd}$ zone was produced on $SiO_2$ supports having a BET surface area of 220 $m^2/g$ and a Pd and Au content of 2.3% by weight in each case.

| Designation | $1^{st}$ Zone | $2^{nd}$ Zone | $3^{rd}$ Zone |
|---|---|---|---|
| relative length [%] | 60 | 40 | — |
| $SiO_2$ support BET ($m^2/g$) | 180 | 220 | — |
| Pd (% by weight) | 2.0 | 2.3 | — |
| Au (% by weight) | 2.0 | 2.3 | — |
| K (% by weight) | 6.5 | 3.0 | — |

This catalyst system according to the invention makes it possible to achieve maximum space-time yields of 1200 g (VAM)/l of cat.*h at ethene selectivies of 94.0% in the test in the reactor under the conditions described.

EXAMPLE 4

Three Catalyst Zones Having Differing Support Geometries

Three catalysts were synthesized as described in WO 2008/071610; these differed in different BET surface areas of the $SiO_2$ supports, EM and potassium contents and also in reduced wall thickness in the $3^{rd}$ zone.

| Designation | $1^{st}$ Zone | $2^{nd}$ Zone | $3^{rd}$ Zone |
|---|---|---|---|
| relative length [%] | 50 | 30 | 20 |
| $SiO_2$ support BET ($m^2/g$) | 200 | 200 | 220 |
| support geometry | rings | rings | rings |
| wall thickness [mm] | 1.8 | 1.8 | 1.3 |
| Pd (% by weight) | 2.0 | 2.3 | 2.6 |
| Au (% by weight) | 2.0 | 2.3 | 2.6 |
| Cd (% by weight) | 0 | 0 | 0 |
| K (% by weight) | 6.5 | 3.5 | 2.0 |

This catalyst system according to the invention makes it possible to achieve maximum space-time yields of 1250 g (VAM)/l of cat.*h at maximum ethene selectivities of 94.5% in the test in the reactor under the conditions described.

EXAMPLE 5

Two Catalyst Zones Having a Low Wall Thickness

Two catalysts were synthesized as described in WO 2008/071610; these differed in different wall thicknesses of the $SiO_2$ supports and potassium contents.

| Designation | $1^{st}$ Zone | $2^{nd}$ Zone | $3^{rd}$ Zone |
|---|---|---|---|
| relative length [%] | 60 | 40 | — |
| $SiO_2$ support BET ($m^2/g$) | 200 | 200 | — |
| support geometry | rings | rings | — |
| wall thickness [mm] | 0.6 | 1.3 | — |
| Pd (% by weight) | 2.0 | 2.3 | — |
| Au (% by weight) | 2.0 | 2.3 | — |
| Cd (% by weight) | 0 | 0 | — |
| K (% by weight) | 5.5 | 2.5 | — |

This catalyst system according to the invention made it possible to achieve maximum space-time yields of 1100 g (VAM)/l of cat.*h at maximum ethene selectivities of 94.0% in the test in the reactor under the conditions described.

COMPARATIVE EXAMPLE 1

Pd/Au Type Catalyst

A catalyst was produced in accordance with the description in WO 2008/071610, said catalyst having the following composition:

| Designation | $1^{st}$ Zone | $2^{nd}$ Zone | $3^{rd}$ Zone |
|---|---|---|---|
| relative length [%] | 100 | — | — |
| $SiO_2$ support BET ($m^2/g$) | 200 | — | — |
| Pd (% by weight) | 2.0 | — | — |
| Au (% by weight) | 2.0 | — | — |
| K (% by weight) | 6.5 | — | — |

This (one-zone) catalyst which is not according to the invention makes it possible to achieve maximum space-time yields of 850 g (VAM)/l of cat.*h at maximum ethene selectivities of 92.0% in the test in the reactor under the test conditions described.

Figure 2:
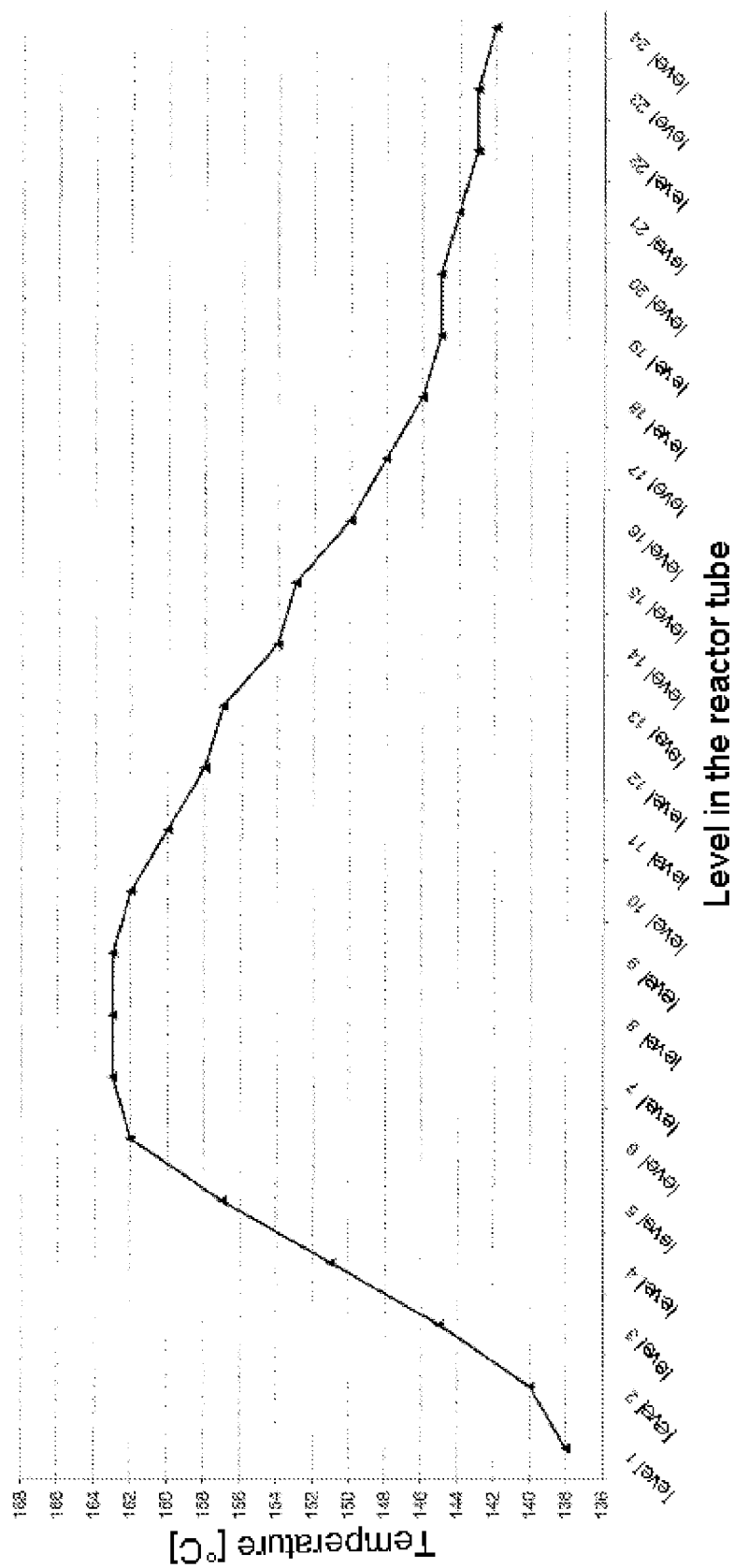
FIG. 2 illustrates the temperature of a prior art acetoxylation reactor having but a single, uniform catalyst bed.

FIG. 2 shows the temperature profile of a catalyst which is not according to the invention (one-zone) with clear formation of a hot spot in the upstream reactor region. The temperature profile shows the one-zone catalyst system at 7.5% by volume of $O_2$, 4500 standard $m^3/(m^3*h)$ and a gas entry temperature of 138° C.

The results of the individual examples (Ex.) and comparative examples (Com. ex.) are shown in Table 1.

TABLE 1

| Designation | Com. ex. 1 | Ex. 1 | Ex. 2 | Ex. 3 | Ex. 4 | Ex. 5 |
|---|---|---|---|---|---|---|
| Catalyst fill height [%] | | | | | | |
| 1$^{st}$ zone | 100 | 50 | 50 | 60 | 50 | 60 |
| 2$^{nd}$ zone | — | 50 | 50 | 40 | 30 | 40 |
| 3$^{rd}$ zone | — | — | — | — | 20 | — |
| STY g (VAM)/l of cat. * h | 850 | 980 | 1050 | 1200 | 1250 | 1100 |
| ethene selectivity [%] | 92.0 | 93.2 | 93.5 | 94.0 | 94.5 | 94.0 |
| Hot Spot [° C.] | | | | | | |
| 1$^{st}$ zone | 163 | 164 | 164 | 170 | 172 | 165 |
| 2$^{nd}$ zone | — | 163 | 163 | 163 | 166 | 162 |
| 3$^{rd}$ zone | — | — | — | — | 164 | — |

The invention claimed is:

1. A process for the acetoxylation of olefins in a gaseous reaction stream containing an olefin, acetic acid and an oxygen-containing gas, comprising passing a reaction gas comprising at least one olefin, oxygen, and acetic acid over at least two fixed catalyst zones of supported olefin acetoxylation catalysts of differing reactivity arranged in series, wherein the catalyst zones are located in one or more reaction tubes arranged in parallel.

2. The process of claim 1, wherein molecular oxygen is used as oxygen-containing gas.

3. The process of claim 1, wherein ethene and acetic acid are reacted to form vinyl acetate monomer.

4. The process of claim 1, wherein the catalyst zone nearest a reaction gas entry has a lower activity and adjoining catalyst zones have an increasing activity in order through to a gas exit.

5. The process of claim 1, wherein the activity of the individual catalyst zones is controlled by means of one or more of the following measures:
   a) varying a content of potassium acetate, lithium acetate, sodium acetate, cesium acetate, rubidium acetate or their mixtures as activity-controlling promoters in the catalyst;
   b) varying a metal content of gold, palladium, and/or cadmium in the catalyst;
   c) varying the mixing ratio of noble metals, contained in the catalyst;
   d) varying a BET surface area of a catalyst support;
   e) varying the bulk density of a catalyst support;
   f) varying a catalyst support geometry;
   g) employing different metals as a catalyst component;
   h) diluting an olefin acetoxylation catalyst with an inert material;
   i) varying an acidity and/or a hydrophilicity of a catalyst support;
   j) varying a thickness of an active noble metal layer on a catalyst support.

6. The process of claim 1, wherein a shape of a catalyst support in one or more catalyst zones is in the form of spheres, cylinders, rings, shaped bodies having one or more through-channels, crown rings, wagon wheels, monoliths, trilobes or tetralobes.

7. The process of claim 6, wherein rings having a wall thickness of less than 2 mm are used as catalyst supports.

8. The process of claim 1, wherein the catalysts are present on $SiO_2$ supports or mixed oxide supports, the metal oxides being of natural origin or pyrogenically produced.

9. The process of claim 1, wherein two catalyst zones are employed, and a first catalyst in a first catalyst zone nearest an inlet for the reaction gas has a lower activity than a second catalyst in a second catalyst zone downstream from the first catalyst zone.

* * * * *

UNITED STATES PATENT AND TRADEMARK OFFICE
CERTIFICATE OF CORRECTION

| | | |
|---|---|---|
| PATENT NO. | : 8,907,123 B2 | Page 1 of 1 |
| APPLICATION NO. | : 14/240945 | |
| DATED | : December 9, 2014 | |
| INVENTOR(S) | : Roscher et al. | |

It is certified that error appears in the above-identified patent and that said Letters Patent is hereby corrected as shown below:

In the Claim

Column 10, Line 10, Claim 5:

After "c) varying"
Delete "the" and
Insert -- a --.

Column 10, Line 13, Claim 5:

After "e) varying"
Delete "the" and
Insert -- a --.

Signed and Sealed this
Thirty-first Day of March, 2015

Michelle K. Lee
*Director of the United States Patent and Trademark Office*